(12) United States Patent
Shen et al.

(10) Patent No.: US 11,944,746 B2
(45) Date of Patent: Apr. 2, 2024

(54) FLUID DELIVERY APPARATUS (71) Applicant: MICROBASE TECHNOLOGY CORP., Taoyuan (TW)

(72) Inventors: Chiu-Ju Shen, Taoyuan (TW); Po Chuan Chen, Taoyuan (TW); Jo Ling Wu, Taoyuan (TW)

(73) Assignee: MICROBASE TECHNOLOGY CORP., Taoyuan (TW)

( * ) Notice: Subject to any disclaimer, the term of this patent is extended or adjusted under 35 U.S.C. 154(b) by 634 days.

(21) Appl. No.: 16/759,739

(22) PCT Filed: Nov. 5, 2018

(86) PCT No.: PCT/CN2018/114010
§ 371 (c)(1),
(2) Date: Apr. 28, 2020

(87) PCT Pub. No.: WO2019/086036
PCT Pub. Date: May 9, 2019

(65) Prior Publication Data
US 2021/0369990 A1 Dec. 2, 2021

Related U.S. Application Data (60) Provisional application No. 62/581,796, filed on Nov. 6, 2017.

(51) Int. Cl.
*A61M 15/00* (2006.01)
*A61M 11/00* (2006.01)

(52) U.S. Cl.
CPC ...... *A61M 15/0065* (2013.01); *A61M 11/007* (2014.02); *A61M 2202/0468* (2013.01)

(58) Field of Classification Search
CPC .................. A61M 15/0065; A61M 11/007; A61M 11/00; A61M 11/02; A61M 11/06; A61M 15/0036; A61M 15/009
See application file for complete search history.

(56) References Cited

U.S. PATENT DOCUMENTS

| | | | | |
|---|---|---|---|---|
| 3,283,959 A | * | 11/1966 | Muller | B65D 83/14 222/396 |
| 2007/0282276 A1 | * | 12/2007 | Boeck | F04B 53/16 604/207 |

(Continued)

FOREIGN PATENT DOCUMENTS

| CN | 101300041 A | 11/2008 |
|---|---|---|
| CN | 206299793 U | 7/2017 |

OTHER PUBLICATIONS

Extended European search report from EPO, dated Jul. 23, 2021.
(Continued)

*Primary Examiner* — Brandy S Lee
*Assistant Examiner* — Hong-Van N Trinh
(74) *Attorney, Agent, or Firm* — Laurence Kao; OPES IP Consulting Co., Ltd.

(57) ABSTRACT

A fluid delivery apparatus comprises a first piston body, a second piston body, a fluid delivery pipe, and a sealing element. The first piston body has a first through hole, a first connecting portion, an accommodation space and a buffer space. The second piston body has a second through hole and a second connecting portion disposed inside the accommodation space. The fluid delivery pipe is accommodated in the first through hole and the second through hole, and movable between a first position and a second position. The sealing element encircles the fluid delivery pipe. When the fluid delivery pipe is at the first position, the sealing element is accommodated in the accommodation space. When the fluid delivery pipe is at the second position, a first part of the sealing element is accommodated in the accommodation space, and a second part of the sealing element is accommodated in the buffer space.

9 Claims, 12 Drawing Sheets

(56) References Cited

U.S. PATENT DOCUMENTS

2012/0174919 A1     7/2012   Hausmann et al.
2012/0325204 A1*  12/2012   Holakovsky ........ B05B 11/1091
                                                         128/200.23

OTHER PUBLICATIONS

Zhenshan Huang, International search report and written opinion by CNIPA as the International search authority, dated Jan. 30, 2019.

* cited by examiner

FLUID DELIVERY APPARATUS

CROSS REFERENCE TO RELATED APPLICATION

The present application claims priority to PCT Application PCT/CN2018/114010 filed on Nov. 5, 2018, which claims priority to U.S. Provisional Application Ser. No. 62/581,796 filed on, Nov. 6, 2017, and the entire content of which is incorporated by reference to this application.

FIELD

The present disclosure relates to a fluid delivery apparatus, and more particularly to a fluid delivery apparatus for delivering medication liquid.

BACKGROUND

Aerosolizer, also known as nebulizer or atomizer, is used to deliver medication to patients for inhalation. Particularly, liquid medicament is broken down into aerosol having fine particles/droplets for easier and more efficient inhalation and absorption. The particle size may be adjusted depending on different respiratory conditions, such as Chronic Obstructive Pulmonary Disease (COPD) or asthma, or depending on the requirement of the liquid medicament itself. Receiving the same precise amount of medication in each treatment is also very important for patients. In other words, an ideal aerosolizer should be able to deliver a precise dosage of medication having a fixed average particle size in every respective operation to reduce waste and risks of overdosing.

The traditional aerosolizer usually utilizes a piston pump to deliver the precise dosage of medication. However, if the piston pump and the corresponding piston body cannot seal the liquid medicament, the aerosolizer likely cannot deliver the precise dosage of medication, at least due to, e.g., leakage. Consequently, the working life of the aerosolizer might be reduced. Therefore, it is important to improve the sealing efficiency between the piston pump and the corresponding piston body.

SUMMARY

The present disclosure provides a fluid delivery apparatus having the improved structure of a piston body, and the sealing between the piston pump and the piston body efficiency can be improved when a fluid delivery pipe is mounted on such piston body.

The present disclosure discloses a fluid delivery apparatus. The fluid delivery apparatus includes a first piston body, a second piston body, a fluid delivery pipe, and a sealing element. The first piston body has a first through hole and a first connecting portion. An end of the first through hole is exposed to the first connecting portion. The first connecting portion has an accommodation space and a buffer space communicable to the accommodation space. The second piston body, contacting the first piston body, has a second through hole and a second connecting portion. An end of the second through hole is exposed to the second connecting portion, and at least part of the second connecting portion is disposed inside the accommodation space. The fluid delivery pipe, accommodated in the first through hole and the second through hole, is movable between a first position and a second position. The sealing element is configured to encircle the fluid delivery pipe. When the fluid delivery pipe is at the first position, the sealing element is accommodated in the accommodation space. When the fluid delivery pipe is at the second position, a first part of the sealing element is accommodated in the accommodation space, and a second part of the sealing element is accommodated in the buffer space.

In some embodiments, the hardness of the sealing element is in the range between XX to YY, and the compression set of the sealing element is in the range between 8% and 18%. The space occupied by the sealing element is in the range between 78% and 94% of the combination of the accommodation space and the buffer space. In addition, the first connecting portion has a side surface, a supporting surface, and an inclined surface. The supporting surface is adjacent to the side surface and the inclined surface. The accommodation space is defined by the side surface and the supporting surface. The buffer space is defined by the inclined surface and the supporting surface.

In some embodiments, the second connecting portion can further have a positioning recess at an upper surface of the second connecting portion, for accommodating part of the sealing element. In addition, the width of the positioning recess is in the range between 0.6 mm and 1 mm.

The present disclosure also discloses another fluid delivery apparatus. The fluid delivery apparatus includes a sealing element, a first piston body, and a second piston body. The first piston body has a first connecting portion, having a supporting surface. The supporting surface contacts the sealing element. The second piston body has a second connecting portion, and the second connecting portion contacts the first connecting portion and has an upper surface. The upper surface contacts the sealing element. The sealing element is disposed between the first piston body and the second piston body. The upper surface is parallel to the supporting surface. The area of the upper surface is larger than the area of the supporting surface.

In some embodiments, the fluid delivery apparatus can further include a fluid delivery pipe, and the fluid delivery pipe is accommodated by the sealing element, a first through hole of the first piston body, and a second through hole of the second piston body. In addition, the fluid delivery pipe is movable between a first position and a second position. When the fluid delivery pipe is at the first position, the sealing element is accommodated between the supporting surface and the upper surface. When the fluid delivery pipe is at the second position, a first part of the sealing element is accommodated between the supporting surface and the upper surface, and a second part of the sealing element protrudes from the supporting surface. Besides, the area of the supporting surface is in the range between 60% and 85% of the area of the upper surface.

As a result, the disclosed fluid delivery apparatus provides the improved structure of a piston body, which can lower the stress of the sealing element and maintain sealing efficiency while the fluid delivery pipe pumps liquid.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the disclosure. Any reference signs in the claims shall not be construed as limiting the scope. Like reference symbols in the various drawings indicate like elements.

DETAILED DESCRIPTION OF THE DISCLOSURE

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Throughout the various views and illustrative embodiments, like reference numerals are used to designate like elements. Reference will now be made in detail to exemplary embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, an apparatus in accordance with the present disclosure. It is to be understood that elements not specifically shown or described may take various forms. Reference throughout this specification to "one embodiment" or "some embodiments" means that a particular feature, structure, or characteristic described in connection with the embodiment is included in at least one embodiment. Thus, the appearances of the phrases "in one embodiment" or "in some embodiments" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are merely intended for illustration.

In the drawings, like reference numbers are used to designate like or similar elements throughout the various views, and illustrative embodiments of the present disclosure are shown and described. The figures are not necessarily drawn to scale, and in some instances the drawings have been exaggerated and/or simplified in places for illustrative purposes. One of ordinary skill in the art will appreciate the many possible applications and variations of the present disclosure based on the following illustrative embodiments of the present disclosure.

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise. Furthermore, relative terms, such as "bottom" and "top," may be used herein to describe one element's relationship to other elements as illustrated in the Figures.

It will be understood that elements described as "under" or "below" other elements would then be oriented "over" or "above" the other elements. The exemplary terms "under" or "below" can, therefore, encompass both an orientation of over and under.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 1:
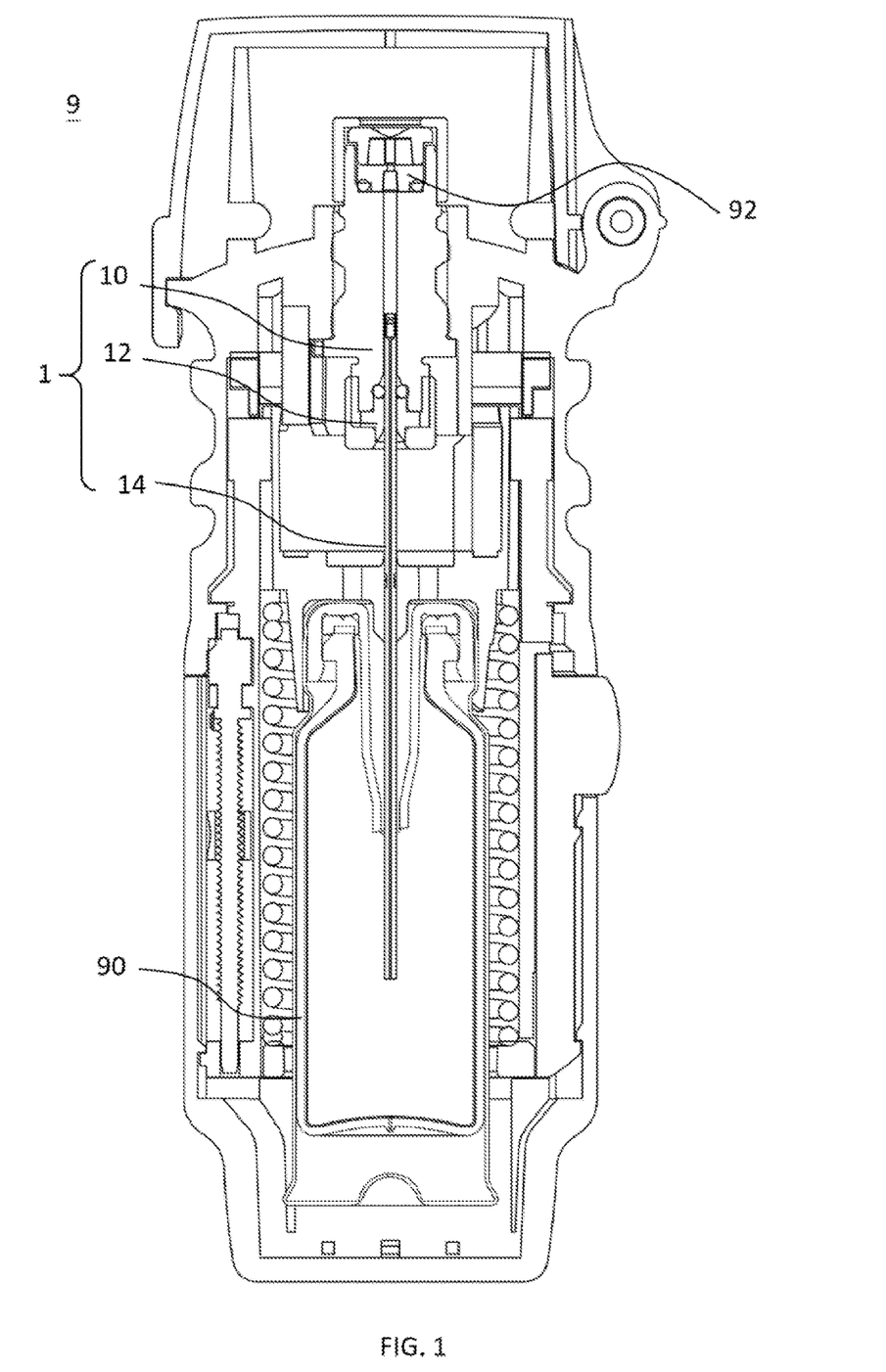
FIG. 1 illustrates a cross section view of the aerosolizer according to some embodiments of the present disclosure.

Please refer to FIG. 1, FIG. 1 illustrates a cross section view of the aerosolizer according to some embodiments of the present disclosure. As shown in FIG. 1, the fluid delivery apparatus 1 could be contained in an aerosolizer 9, having a storage container 90 and a nozzle assembly 92. The fluid delivery apparatus 1 is configured to pump the liquid medicament from the storage container 90 to the nozzle assembly 92 such that the fixed amount of liquid medicament is prepared to be aerosolized. When the aerosolizer 9 is actuated, the fixed amount of liquid medicament can be pushed toward and through the nozzle assembly 92, thereby creating the aerosol for inhalation. In one example, when the aerosolizer 9 is assembled, one end of the fluid delivery pipe 14 can be positioned in the storage container 90 and the other end of the fluid delivery pipe 14 can be positioned adjacent or correspond to the nozzle assembly 92. Therefore, the liquid medicament can be drawn from the storage container 90 into the nozzle assembly 92 via the fluid delivery pipe 14.

Figure 2:
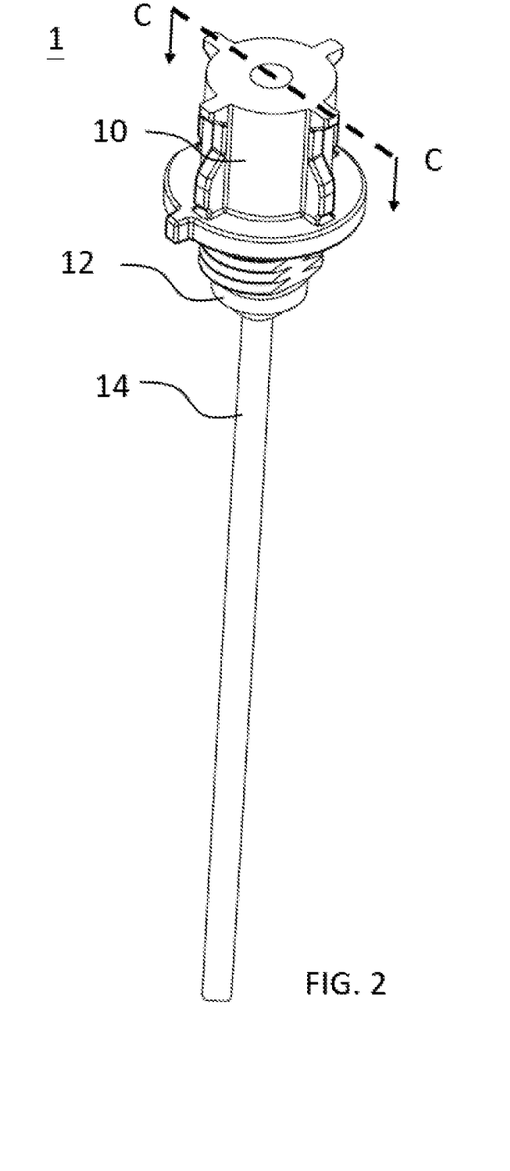
FIG. 2 illustrates a perspective diagram of the fluid delivery apparatus according to some embodiments of the present disclosure.
Figure 3:
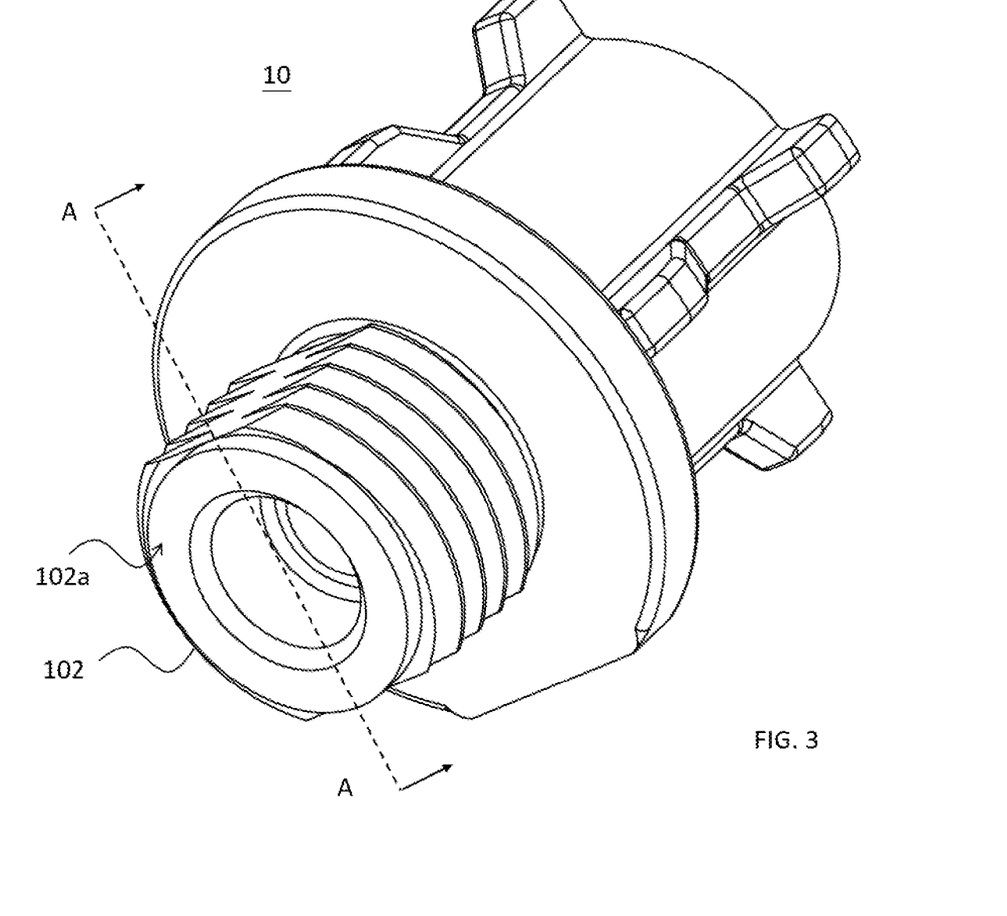
FIG. 3 illustrates a perspective diagram of the first piston body according to some embodiments of the present disclosure.

Please refer to FIG. 2, FIG. 2 illustrates a perspective diagram of the fluid delivery apparatus according to some embodiments of the present disclosure. As shown in FIG. 2, the fluid delivery apparatus 1 includes a first piston body 10, a second piston body 12, and a fluid delivery pipe 14. The fluid delivery pipe 14 is assembled with the first piston body 10 and the second piston body 12. The first piston body 10 includes an accommodation space and a buffer space. At least part of the second piston body 12 can be received by the accommodation space. The disclosure neither limits the shape of the accommodation space nor the shape of the buffer space. It is important that the accommodation space and the buffer space are communicable, and that the buffer space provides additional space to contain a sealing element (not shown in FIG. 2) when the fluid delivery pipe 14 is moving during actuation of the aerosolizer.

Figure 7:
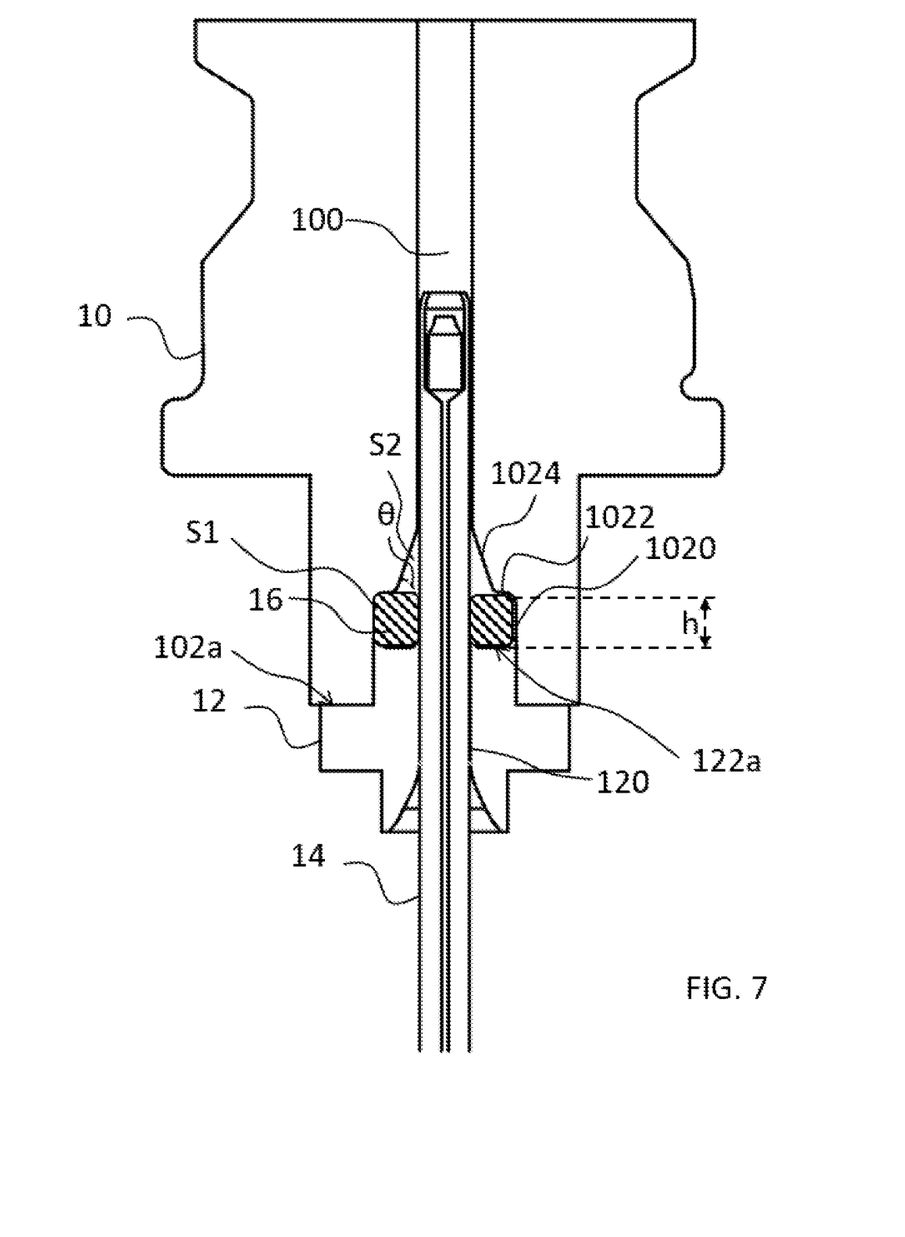
FIG. 7 illustrates a cross section view along CC line of a part of the fluid delivery apparatus according to some embodiments of the present disclosure.
Figure 8:
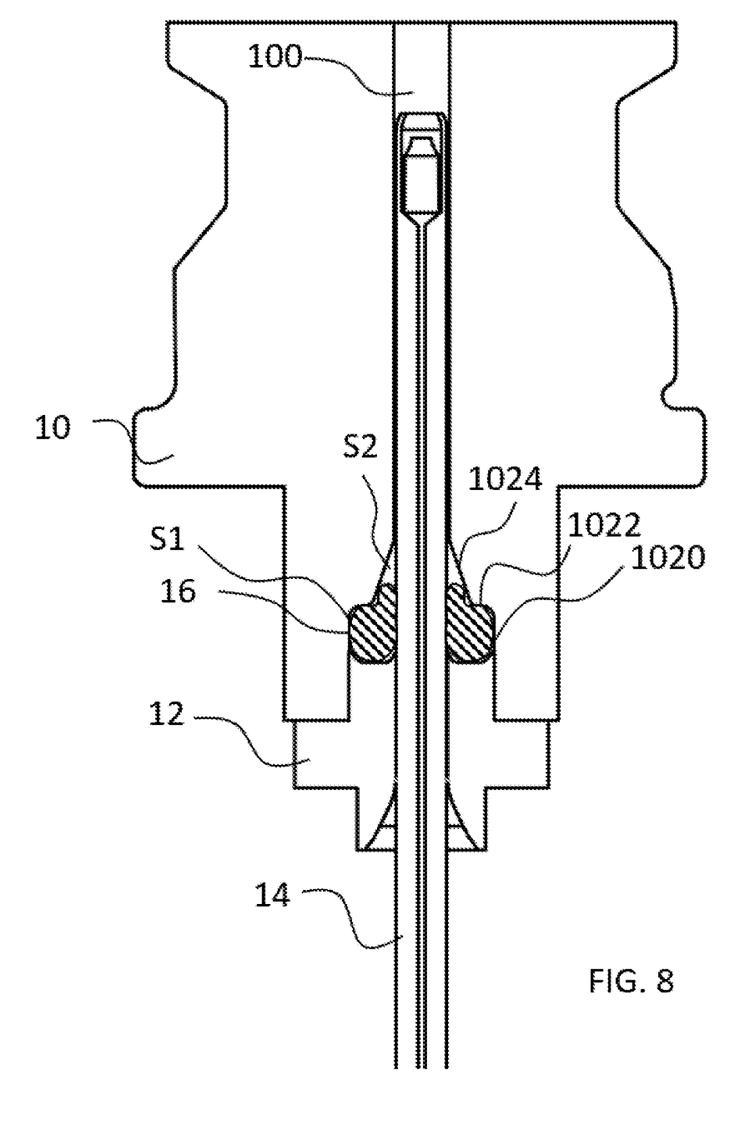
FIG. 8 illustrates a different position of the fluid delivery pipe shown in FIG. 6 according to some embodiments of the present disclosure.

In order to explain the structure of the first piston body 10, please refer to FIG. 3 and FIG. 4. FIG. 3 illustrates a perspective diagram of the first piston body according to some embodiments of the present disclosure, and FIG. 4 illustrates a cross section view along AA line of the first piston body according to some embodiments of the present disclosure. FIG. 3 and FIG. 4 provide an example of the shape of the accommodation space and the shape of the buffer space. As shown in the figures, the first piston body 10 has a first through hole 100 and a first connecting portion 102, and an end of the first through hole 100 corresponds to an opening of the first connecting portion 102. In one example, the first through hole 100 can be circular, and the outer diameter of the fluid delivery pipe 14 can be smaller than the diameter of the first through hole 100. Therefore, the fluid delivery pipe 14 can be received by the first through hole 100. In addition, the first connecting portion 102 can have a top surface **102*a* facing the storage container, and the top surface 102*a* is indented and extends inwardly and connected to the first through hole 100. In practice, the recess of the top surface 102*a* can be considered as one end of the first through hole 100, and the diameter of the recess of the top surface 102*a* can be larger than the diameter of the first through hole 100. Besides, the first piston body 10 can have some structure used for fixing the first piston body 10 inside the aerosolizer. For example, the outer surface of the first piston body 10** can have, but not limited to, thread grooves.

FIG. 4 shows the inner structure of the first connecting portion 102. The inner surface of the first connecting portion 102 can be defined separately as a side surface 1020, a supporting surface 1022, and an inclined surface 1024. The inclined surface 1024 connects the inner surface of the first through hole 100, and the supporting surface 1022 is defined between the side surface 1020 and the inclined surface 1024. The side surface 1020 is an enclosed, i.e., continuously circumferenced, surface located between the top surface **102*a* and the supporting surface 1022, and the space defined by the side surface 1020 therebetween can be defined as an accommodation space S1. Similarly, the inclined surface 1024 is also an enclosed, i.e., continuously circumferenced, surface located between the first through hole 100 and the supporting surface 1022, and the space defined by the inclined surface 1024 therebetween can be defined as a buffer space S2. It is not necessary to have obvious boundaries to separate the accommodation space S1, the buffer space S2, and the first through hole 100. In the example shown in FIG. 4, the accommodation space S1, the buffer space S2, and the first through hole 100 are communicable and continuous, and the buffer space S2 and the first through hole 100 are adjacent to each other. The volume of the accommodation space S1 can be larger than the volume of the buffer space S2. In one example, when the first piston body 10 and the second piston body 12*a* are assembled, a volume ratio of the buffer space and the accommodation space between the supporting surface 1022 and an upper surface of a second connecting portion (not shown in FIG. 4**) may be, but not limited to, in the range between 0.2 to 0.4.

Please refer to FIG. 5 and FIG. 6, FIG. 5 illustrates a perspective diagram of the second piston body according to some embodiments of the present disclosure, and FIG. 6 illustrates a cross section view along BB line of the second piston body according to some embodiments of the present disclosure. As shown in the figures, the second piston body 12 has a second through hole 120 and a second connecting portion 122, and an end of the second through hole 120 corresponds to an opening of the second connecting portion 122. The second through hole 120 can also be circular, and the diameter of the second through hole 120 is substantially the same as the diameter of the first through hole 100. Besides, the outer diameter of the fluid delivery pipe 14 can be smaller than the diameter of the second through hole 120. Therefore, the fluid delivery pipe 14 can be received by the second through hole 120. The second piston body 12 has a bottom surface **12*a*, and the second connecting portion 122 protrudes from the bottom surface 12*a*. The second connecting portion 122 can have an upper surface 122*a*, non-coplanar to the bottom surface 12*a*, and the upper surface 122*a* can be within the peripheral of the bottom surface 12*a*, i.e., the diameter of the upper surface 122*a* is smaller than that of the bottom surface 12*a***.

When the first piston body 10 and the second piston body 12 are assembled, the first through hole 100 and the second through hole 120 share the same axis so that the fluid delivery pipe 14 can be received by the first through hole 100 and the second through hole 120 at the same time. Also, the fluid delivery pipe 14 is so configured to be movable within the first through hole 100 and the second through hole 120. In addition, at least part of the second connecting portion 122 can be disposed inside the accommodation space S1, and at least part of the side surface 1020 of the first connecting portion 102 can closely contact the outer surface of the second connecting portion 122. Said "closely contact" can be, but not limited to, "interference fit" or "close fit". The bottom surface **12*a* of the second piston body 12 can abut against the top surface 102*a* of the first connecting portion 102 to prevent the second connecting portion 122 from being overly pushed into the accommodation space S1. As a result, a fixed volume of the accommodation space S1** can be maintained.

In some embodiments, the second piston body 12 may include a positioning recess 1220 surrounding the second through hole 120. In one example, the positioning recess 1220 can be formed within the peripheral of the upper surface **122*a*, and can be a groove. In one example, the bottom of the positioning recess 1220 can be a flat surface. Moreover the positioning recess 1220 can have protrusion structure at its exterior peripheral, meaning that the depth of the positioning recess 1220 might not be constant. The depth of the positioning recess 1220 at its exterior peripheral can be smaller than the depth of the positioning recess 1220 around the center. Said "depth" can be considered as the distance between the bottom of the positioning recess 1220 and the upper surface 122*a*. The positioning recess 1220 can also be considered as a part of the upper surface 122*a* curved inwardly. In other words, the upper surface 122*a*** is not necessary a flat surface.

In order to explain the structure of the fluid delivery apparatus 1, please refer to FIG. 2, FIG. 7 and FIG. 8, FIG. 7 illustrates a cross section view along CC line of a part of the fluid delivery apparatus according to some embodiments of the present disclosure, and FIG. 8 illustrates a different position of the fluid delivery pipe shown in FIG. 7 according to some embodiments of the present disclosure. The difference between FIG. 7 and FIG. 8 is the position of the fluid delivery pipe 14. For example, the fluid delivery pipe 14 could be at a first position in FIG. 7 and at a second position in FIG. 8. As shown in the figures, the fluid delivery apparatus 1 can have a sealing element 16 disposed in the accommodation space S1, encircling the fluid delivery pipe 14. In addition, FIG. 7 and FIG. 8 show that the side surface 1020 is substantially perpendicular to the top surface 102a, the supporting surface 1022 is substantially perpendicular to the side surface 1020, and the supporting surface 1022 is substantially parallel to the top surface 102a. In the example shown in FIG. 7, the supporting surface 1022 is smaller in diameter than the top surface 102a. The inclined surface 1024 inclines continuously inwardly from the supporting surface 1022 towards the center of the first piston body 10 and therefore is within the peripheral of the supporting surface 1022. In other words, the inclined surface 1024 in smaller in dimension than the supporting surface 1022. Moreover, the first through hole 100 is within the peripheral of the inclined surface 1024. In some embodiments, an angle θ can be defined between the inclined surface 1024 and the supporting surface 1022. The combination of the first through hole 100 and the second through hole 120 can be considered as a funnel, and the opening of the funnel can be the opening of the first connecting portion 102 on the top surface 102a.

In the example shown in FIG. 7, the aerosolizer is not actuated and the fluid delivery pipe 14 is at a first position, i.e., its static position. Here, the sealing element 16 is yet to be dislocated by the fluid delivery pipe 14 from its static position, and the sealing element 16 has no obvious deformation. Therefore, the sealing element 16 is accommodated in the accommodation space S1. In other words, when the fluid delivery pipe 14 is at the first position, the sealing element 16 is accommodated between the supporting surface 1022 and the upper surface 122a. In the example shown in FIG. 8, the aerosolizer is actuated and the fluid delivery pipe 14 moves from the first position to a second position. Here, the sealing element 16 is already dislocated by the fluid delivery pipe 14 from its static position, and the sealing element 16 is deformed. Therefore, part of the sealing element 16 (a first part) is accommodated in the accommodation space S1, and part of the sealing element 16 (a second part) is accommodated in the buffer space S2. In other words, when the fluid delivery pipe 14 is at the second position, part of the sealing element (a first part) 16 is accommodated between the supporting surface 1022 and the upper surface 122a, and part of the sealing element 16 (a second part) protrudes from the supporting surface 1022 and enters the buffer space S2. The first and second parts may or may not constitute the entire sealing element 16.

FIG. 7 and FIG. 8 demonstrate the movement of the fluid delivery pipe 14 and show the deformation of the sealing element 16 corresponding to an actuation of the nebulizer. It should also be noted that FIG. 7 and FIG. 8 are not configured to limit the exact positions of the fluid delivery pipe 14. The first position and the second position can be the boundary positions of the movement of the fluid delivery pipe 14, and the first position and the second position can also be defined by the shape or location of the sealing element 16. For example, when the sealing element 16 is substantially accommodated in the accommodation space S1, the position of the fluid delivery pipe 14 can be defined as the first position. When the sealing element 16 is accommodated in both the accommodation space S1 and the buffer space S2, the position of the fluid delivery pipe 14 can be defined as the second position.

In one example, when the first piston body 10 and the second piston body 12 are assembled, the sealing element 16 is accommodated between the supporting surface 1022 and the upper surface 122a. If the upper surface 122a has the positioning recess 1220, the sealing element 16 can also be considered as being accommodated between the supporting surface 1022 and the positioning recess 1220. Therefore, the positioning recess 1220 can hold the sealing element 16 in the proper position. With reference to FIG. 7, the distance h between the supporting surface 1022 and the upper surface 122a can be in, but not limited to, the range between 0.8 mm and 1.2 mm. Besides, the area of the upper surface 122a is larger than the area of the supporting surface 1022. Since the supporting surface 1022 is connected to the inclined surface 1024, the projection area, along the axis of the fluid delivery pipe 14, of the combination of the supporting surface 1022 and the inclined surface 1024 is substantially equaled to the projection area of the upper surface 122a.

When the fluid delivery pipe 14 is at the first position, the sealing element 16 can closely contact the outer surface of the fluid delivery pipe 14 and the side surface 1020 of the first connecting portion 102. Therefore, the sealing element 16 can seal the accommodation space S1 and prevent liquid medicament leakage into the gap between the first through hole 100 and the fluid delivery pipe 14. When the fluid delivery pipe 14 is at the second position, the sealing element 16 can closely contact the outer surface of the fluid delivery pipe 14, the side surface 1020, and the inclined surface 1024 at the same time. Therefore, the sealing element 16 can prevent the liquid medicament from escaping or reflowing. Because the traditional piston body does not have the buffer space, when the fluid delivery pipe is moving or pumping, the fluid delivery pipe squeezes the sealing element that the contact area between the sealing element and the side surface is reduced. As such, the sealing element can hardly prevent the liquid medicament from escaping or reflowing, resulting in lowered sealing efficiency. On the other hand, when the fluid delivery pipe 14 of the present disclosure is moving or pumping, the sealing element 16 can be squeezed/dispositioned into the buffer space S2. Consequently, close contact between the sealing element 16 and the inclined surface 1024 is formed, which serves to provide further sealing effect. Thus, there's lower chance for the liquid medicament to escape/reflow from between the sealing element 16 and the space S1 and the buffer space S2. Besides, the buffer space S2 of the fluid delivery apparatus 1 can prevent sealing element 16 from breaking apart while being squeezed.

Figure 9A:
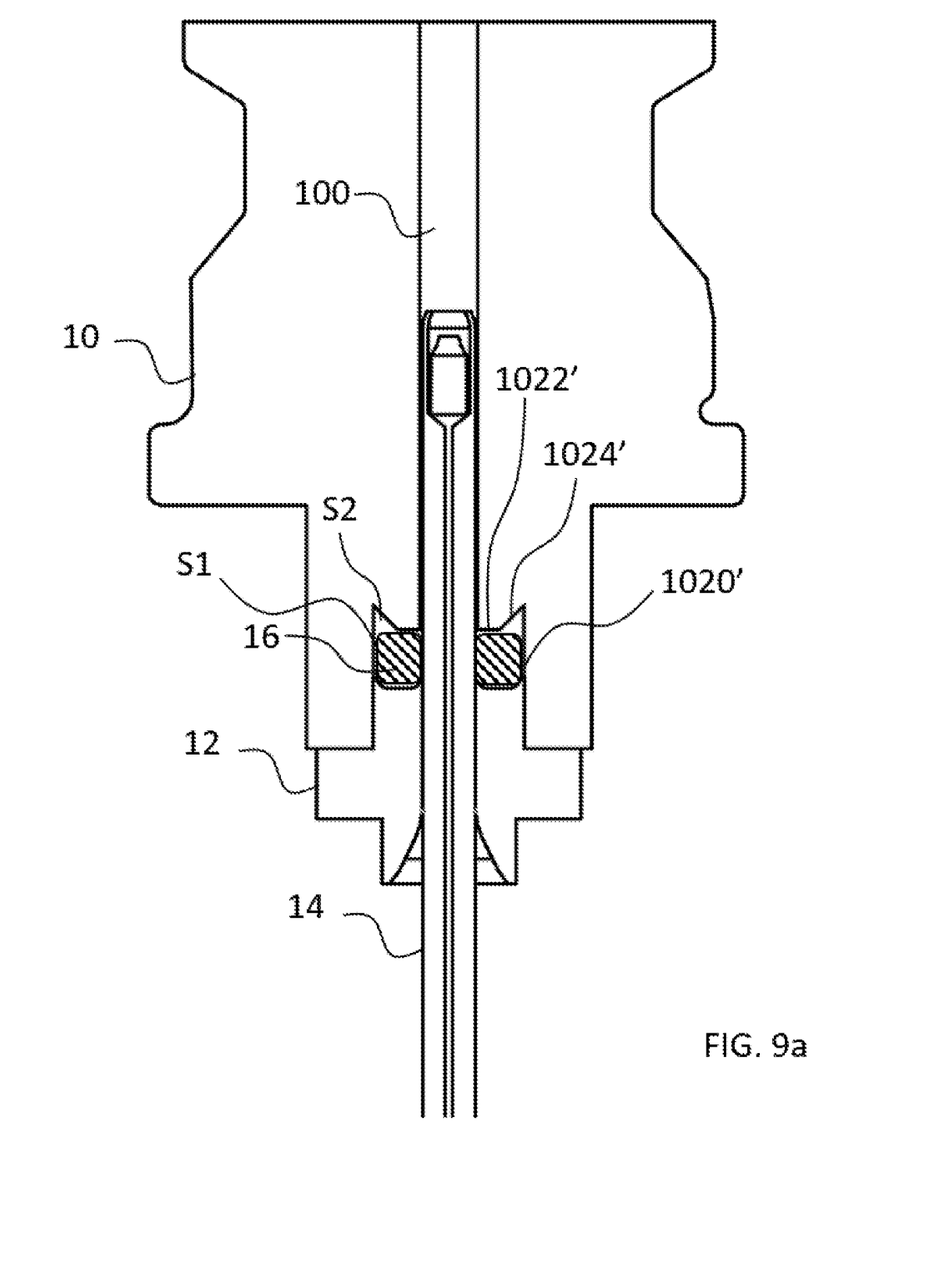
FIG. 9a illustrates a cross section view along CC line of a part of the fluid delivery apparatus according to some other embodiments of the present disclosure.

It should be noted that the inclined surface 1024 does not necessarily connect to the inner surface of the first through hole 100, and the supporting surface 1022 is not necessary defined as between the side surface 1020 and the inclined surface 1024. For example, please refer to FIG. 9a-9c, FIG. 9a illustrates a cross section view along CC line of a part of the fluid delivery apparatus according to some other embodiments of the present disclosure. As shown in FIG. 9a, the inclined surface 1024' can be defined between the side surface 1020' and the supporting surface 1022', and the inclined surface 1024' can face the side surface 1020'. Therefore, the buffer space S2 can be defined as an inner space surrounded by the inclined surface 1024', the side surface 1020', and the supporting surface 1022'. Moreover, the supporting surface 1022' is connected to the inner surface of the first through hole 100. In other words, it shows a different example from FIG. 4 that the buffer space S2 and the first through hole 100 are not adjacent to each other while the accommodation space S1 is still communicable to the buffer space S2 and the first through hole 100.

Figure 9B:
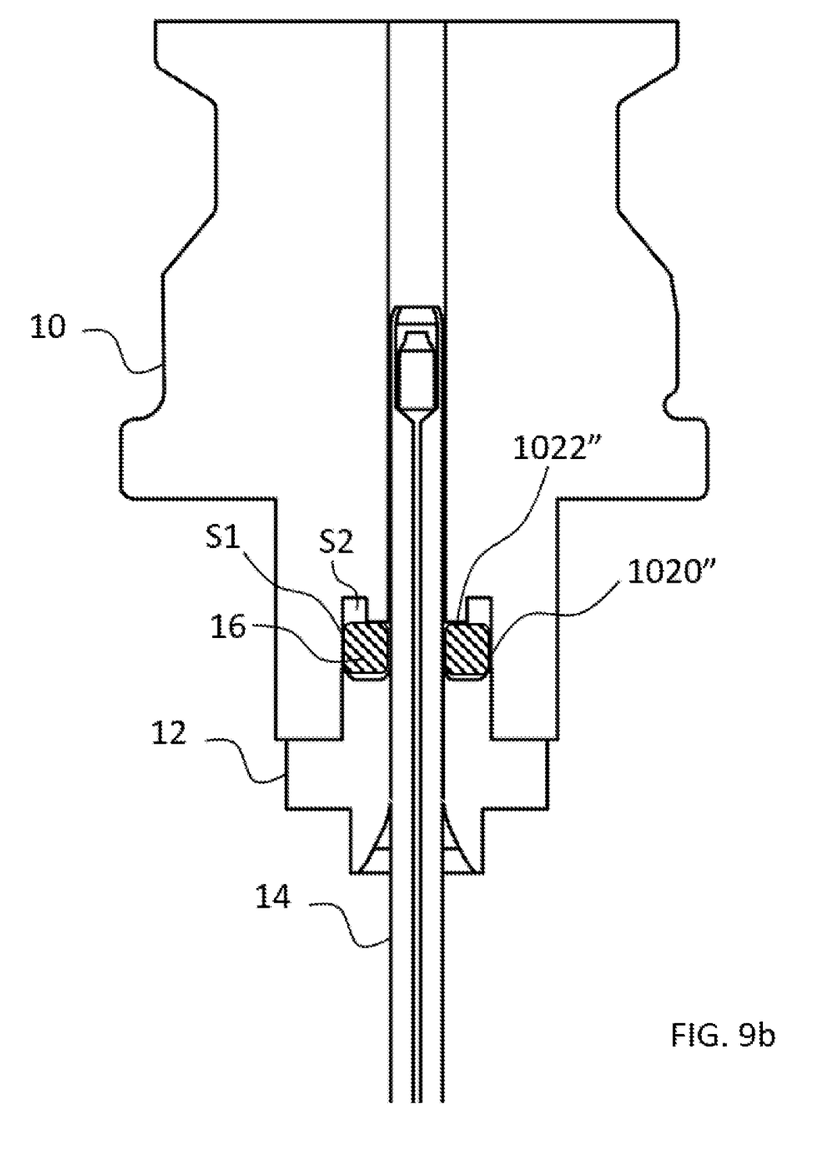
FIG. 9b illustrates a cross section view along CC line of a part of the fluid delivery apparatus according to certain embodiments of the present disclosure.

Also, FIG. 9b illustrates a cross section view along CC line of a part of the fluid delivery apparatus according to certain embodiments of the present disclosure. As shown in FIG. 9b, there is no inclined surface, and the buffer space S2 is not defined by the inclined surface. Specifically, the buffer space S2, which is communicable to the accommodation space S1, can be a randomly shaped recess formed between the supporting surface 1022" and the side surface 1020". As long as the buffer space S2 provides addition space to contain the sealing element 16 when the fluid delivery pipe 14 is not at its first position, the sealing efficiency between the sealing element and the first piston body can be increased.

Figure 9C:
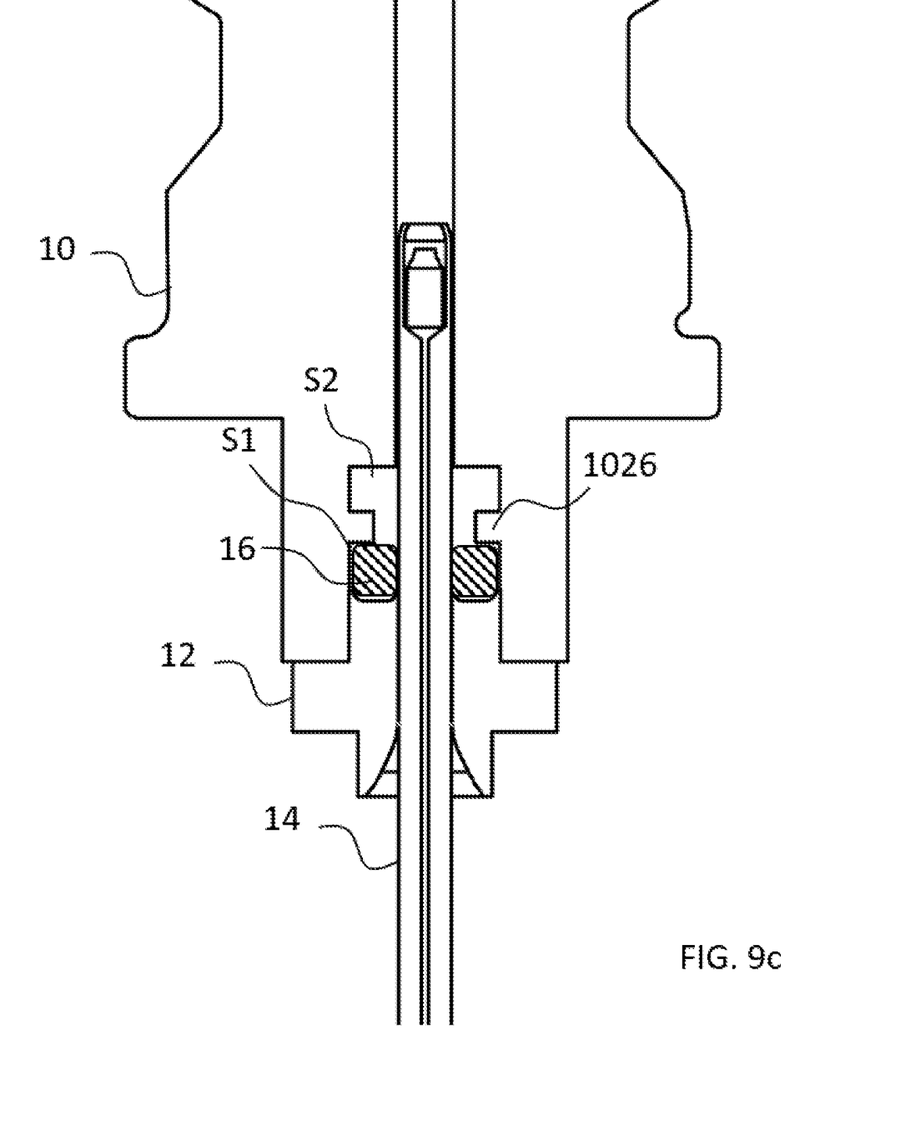
FIG. 9c illustrates a cross section view along CC line of a part of the fluid delivery apparatus according to certain other embodiments of the present disclosure.

FIG. 9c illustrates a cross section view along CC line of a part of the fluid delivery apparatus according to certain other embodiments of the present disclosure. As shown in FIG. 9c, there can be a neck portion 1026 to separate the accommodation space S1 and the buffer space S2. Here, the volume of the buffer space S2 can be adjusted according to different sealing elements. For example, the volume of the buffer space S2 can, but not limited to, substantially equal to the volume of the accommodation space S1 between the supporting surface 1022 and the upper surface 122a.

Figure 4:
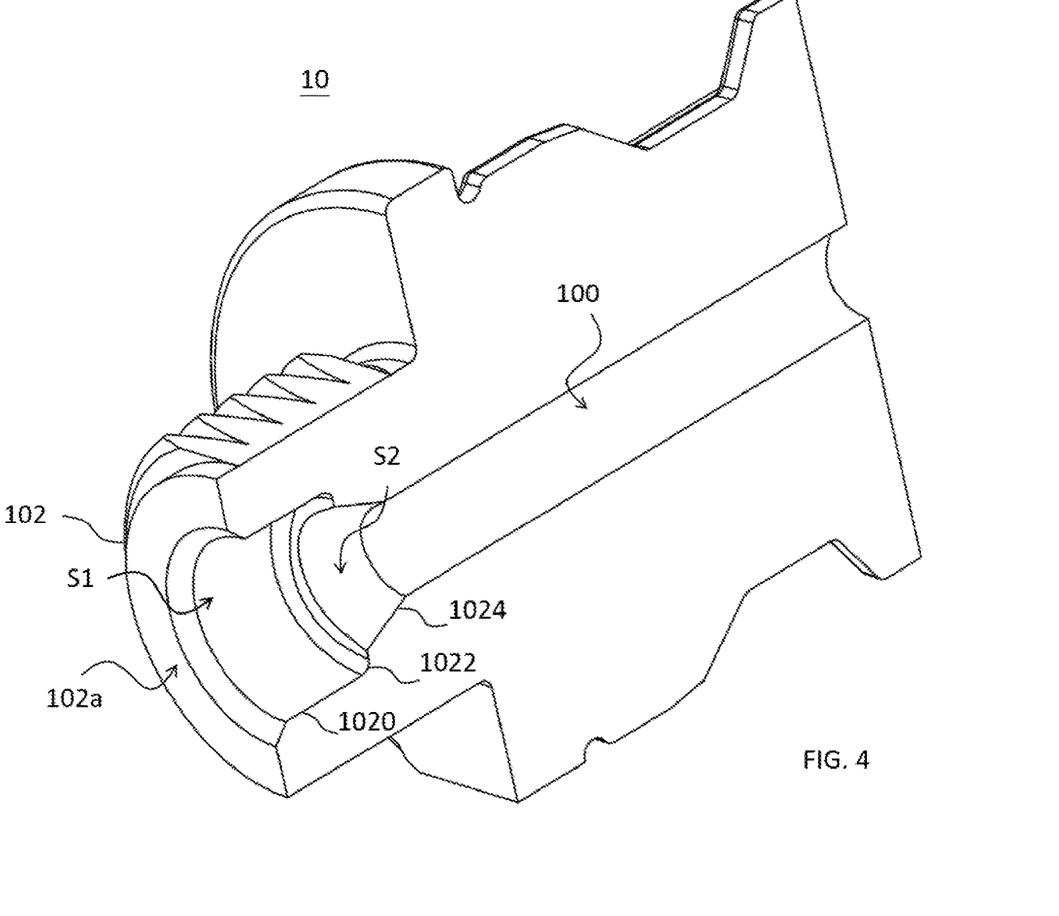
FIG. 4 illustrates a cross section view along AA line of the first piston body according to some embodiments of the present disclosure.
Figure 5:
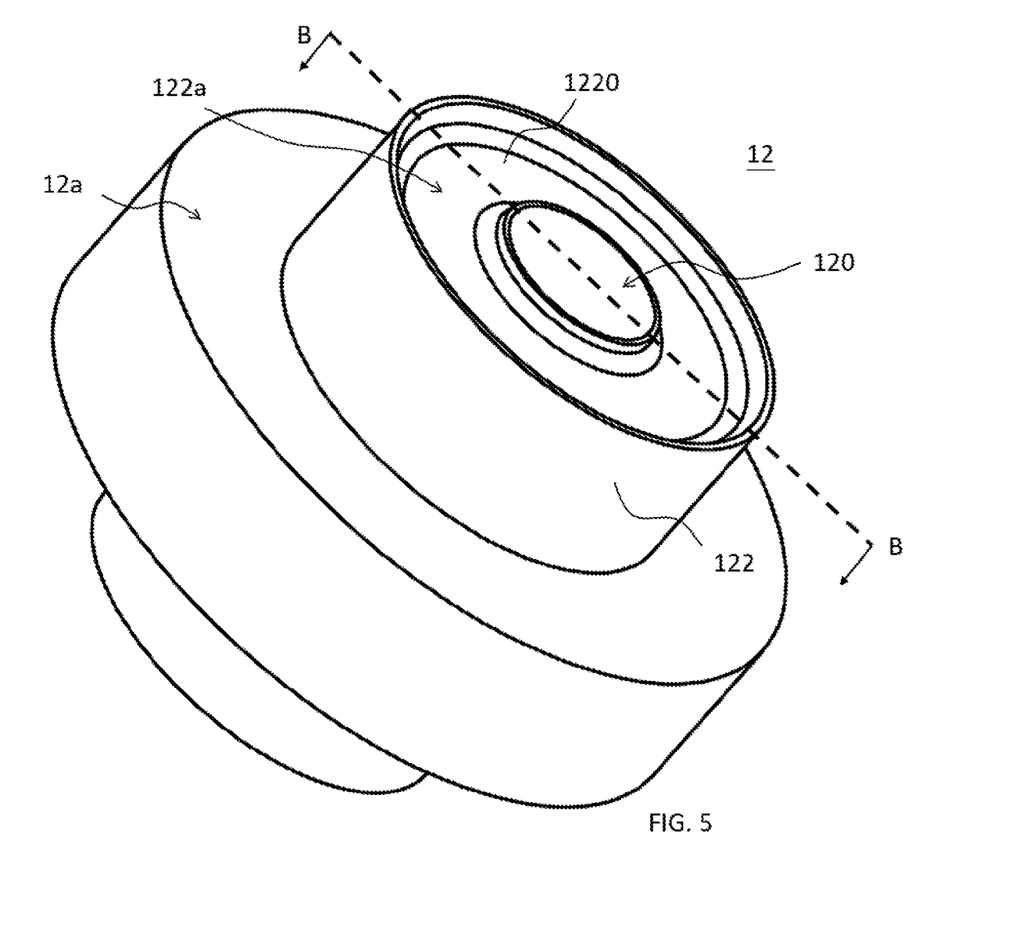
FIG. 5 illustrates a perspective diagram of the second piston body according to some embodiments of the present disclosure.
Figure 6:
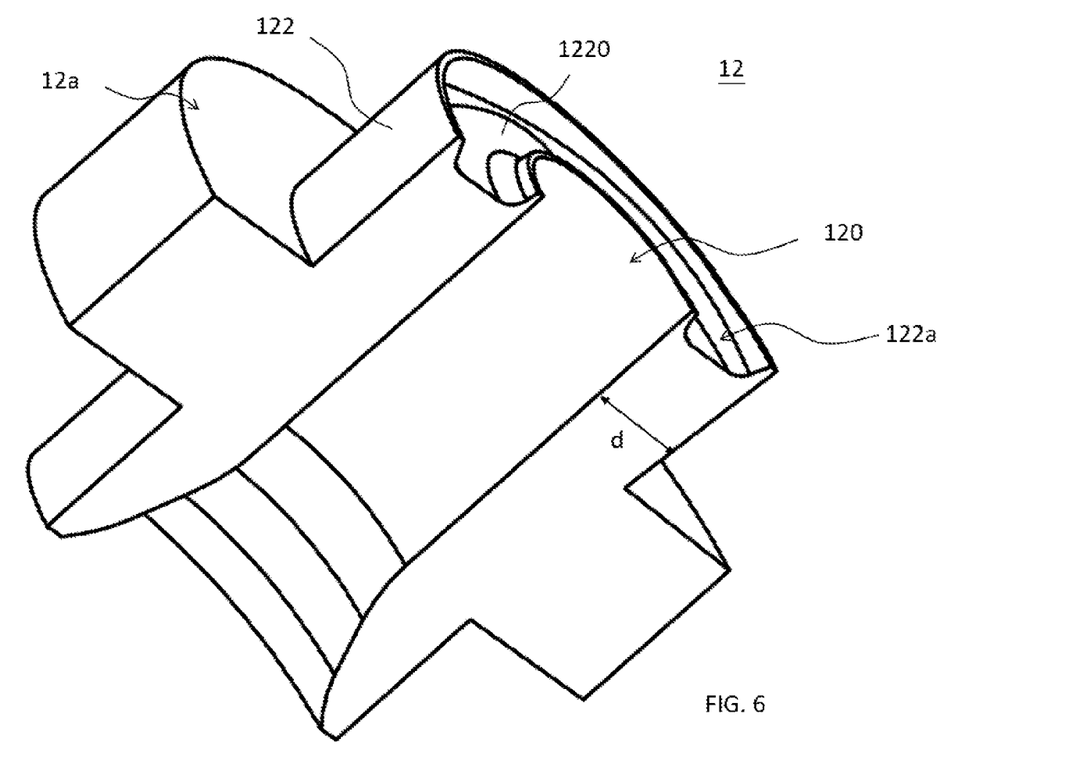
FIG. 6 illustrates a cross section view along BB line of the second piston body according to some embodiments of the present disclosure.
Figure 10:
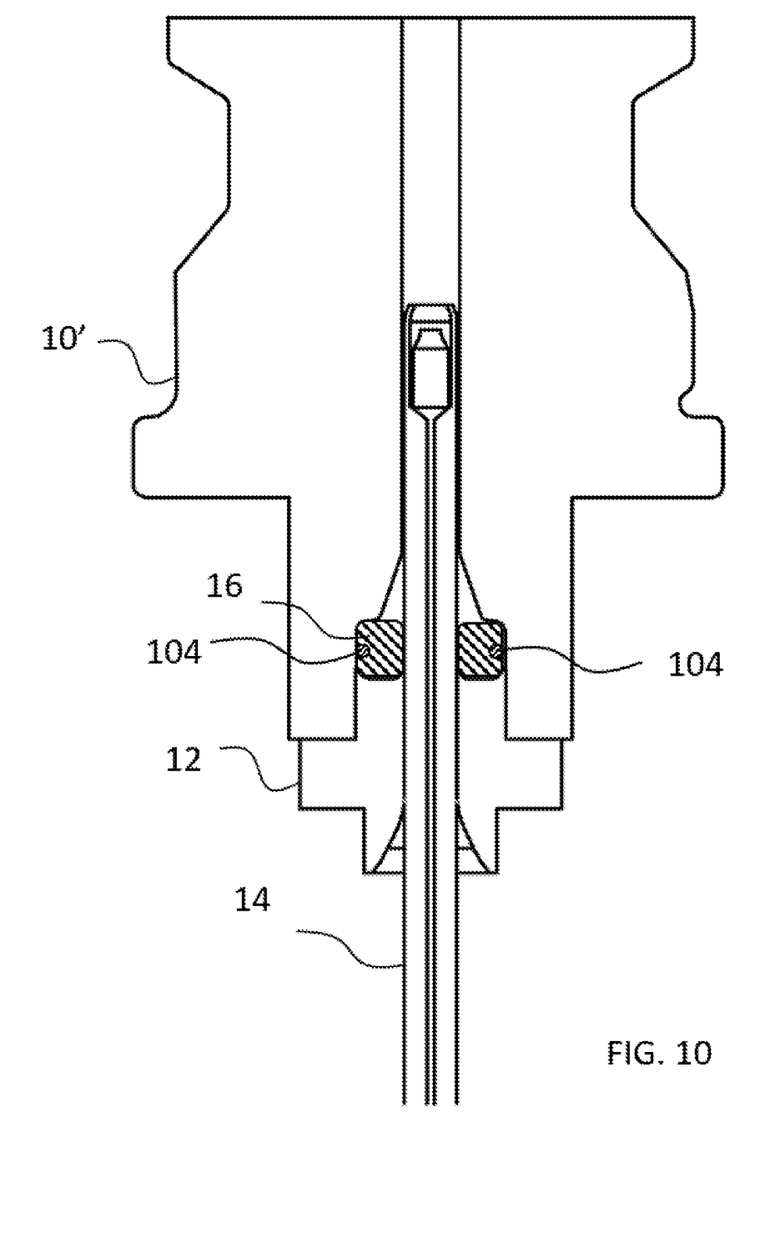
FIG. 10 illustrates a perspective diagram of the fluid delivery apparatus according to another embodiment of the present disclosure.

In some others embodiments of the present disclosure, the first piston body 10 can further include a protrusion. Please refer to FIG. 4 and FIG. 10 FIG. 10 illustrates a perspective diagram of the fluid delivery apparatus according to another embodiment of the present disclosure. As shown in the figures, the first piston body 10' further includes a protrusion 104 at the side surface 1020 and located in the accommodation space S1. The protrusion 104 can be in the form of, but not limited to, a rib surrounding the side surface 1020 or several bumps disposed symmetrically or asymmetrically. In addition, the protrusion 104 and the side surface 1020 can be integrally formed, while the material of the protrusion 104 can be identical as the material of the first piston body 10'. The protrusion 104 can also be mounted on the side surface 1020, while the material of the protrusion 104 can be identical as the material of the sealing element 16. The sealing element 16 can closely contact the protrusion 104 such that the sealing element 16 can be pushed toward the fluid delivery pipe 14 by the protrusion 104. Therefore, the sealing force between the sealing element 16 and the fluid delivery pipe 14 can be increased. As a result, liquid medicament is better prevented from escaping or reflowing between the sealing element 16 and the fluid delivery pipe 14 and the inner surface of the first piston body 10. In other word, sealing efficiency between the piston pump and the corresponding piston body is maintained or improved.

In one example, the sealing element 16 can be a carefully designed O-ring. For example, the sealing element 16 having Shore A hardness between 60 to 80 degree, preferably between 65 to 75 degree. The compression set of the sealing element 16 is in the range between 8% to 18%, preferably between 11% to 15%. The thickness of the sealing element 16 can be in the range between 0.9 mm and 1.3 mm. When the sealing element 16 is yet to be assembled, the volume of the sealing element 16 can be, but not limited to, slightly larger than the volume of the accommodation space S1 between the supporting surface 1022 and the upper surface 122a. When the entire fluid delivery apparatus 1 is assembled, the sealing element 16 can be in the accommodation space S1 between the supporting surface 1022 and the upper surface 122a. The sealing element 16 should be able to encircle the fluid delivery pipe 14, and the space occupied by the sealing element 16 is in the range between 70% to 90% of the combination of the buffer space S2 and the accommodation space S1 between the supporting surface 1022 and the upper surface 122a, preferably between 75% to 85%. Nevertheless, the size of the sealing element 16 is related to the outer diameter of the fluid delivery pipe 14 and the volume of the accommodation space S1.

The fluid delivery apparatus disclosed herein provides an improved structure of the first piston body having a buffer space. Such buffer space serves to lower the stress of the sealing element and provide additional contact area between the sealing element and the first piston body while the fluid delivery pipe pumps liquid during actuation of the aerosolizer. Therefore, the sealing efficiency can be increased.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

LISTING OF ELEMENTS

1 fluid delivery apparatus
10, 10' first piston body
100 first through hole
102 first connecting portion
102*a* top surface
1020 side surface
1022 supporting surface
1024 inclined surface
1026 neck portion
104 protrusion
12 second piston body
12*a* bottom surface
120 second through hole
122 second connecting portion
122*a* upper surface
1220 positioning recess
14 fluid delivery pipe
16 sealing element
S1 accommodation space
S2 buffer space

What is claimed is:

1. A fluid delivery apparatus, comprising:

a first piston body having a first through hole and a first connecting portion, wherein the first through hole extends from one end of the first connecting portion to an opposite end of the first connecting portion, and the first connecting portion has an accommodation space and a buffer space communicable to the accommodation space, wherein the accommodation space is defined by a side surface of the first connecting portion and a supporting surface of the first connecting portion that is substantially perpendicular to the side surface, and the buffer space is located at a distal end of the first connecting portion and the accommodation space is located at a proximal end of the first connecting portion;

a second piston body in contact with the first piston body and having a second through hole and a second connecting portion, wherein the second through hole extends from one end of the second connecting portion to an opposite end of the second connecting portion, and at least part of the second connecting portion is disposed inside the accommodation space;

a fluid delivery pipe, accommodated in the first through hole and the second through hole, and moveable between a first position and a second position; and a sealing element encircling the fluid delivery pipe, wherein when the fluid delivery pipe is at the first position, the sealing element is substantially accommodated in the accommodation space, and when the fluid delivery pipe is disposed at the second position, resulting from its movement towards the first piston body, a first part of the sealing element is accommodated in the accommodation space, and a second part of the sealing element is accommodated in the buffer space.

2. The fluid delivery apparatus according to claim 1, wherein the sealing element has a Shore A hardness between 60 to 80 degrees.

3. The fluid delivery apparatus according to claim 1, wherein a compression set of the sealing element is in the range between 8% and 18%.

4. The fluid delivery apparatus according to claim 1, wherein a volume ratio between the buffer space and the accommodation space between the supporting surface of the first connecting portion and an upper surface of the second connecting portion is in the range between 0.2 to 0.4.

5. The fluid delivery apparatus according to claim 1, wherein the sealing element occupies between 70% and 90% of a total volume of the buffer space and the accommodation space between the supporting surface of the first connecting portion and an upper surface of the second connecting portion.

6. The fluid delivery apparatus according to claim 1, wherein the first connecting portion further has an inclined surface, the supporting surface is adjacent to the side surface and the inclined surface, and the buffer space is defined by the inclined surface and the supporting surface.

7. The fluid delivery apparatus according to claim 1, wherein the second connecting portion further has a positioning recess at an upper surface of the second connecting portion, for accommodating part of the sealing element.

8. The fluid delivery apparatus according to claim 7, wherein a depth of the positioning recess at its exterior peripheral is smaller than a depth of the positioning recess around the center.

9. The fluid delivery apparatus according to claim 1, wherein the first piston body further comprises a protrusion, disposed on the side surface and located in the accommodation space, and the sealing element contacts the protrusion.

* * * * *